United States Patent [19]

Kinugasa et al.

[11] Patent Number: 4,622,181

[45] Date of Patent: Nov. 11, 1986

[54] PROCESS FOR PRODUCING AN ESTRONE ACETAL

[75] Inventors: Kazumasa Kinugasa, Yokohama; Eiichiro Tanaka; Yoshihiro Tanaka, both of Kawasaki; Yoshiharu Morita, Yokohama, all of Japan

[73] Assignee: Mitsubishi Chemical Industries Ltd., Tokyo, Japan

[21] Appl. No.: 662,283

[22] PCT Filed: Feb. 1, 1984

[86] PCT No.: PCT/JP84/00030

§ 371 Date: Sep. 21, 1984

§ 102(e) Date: Sep. 21, 1984

[87] PCT Pub. No.: WO84/03094

PCT Pub. Date: Aug. 16, 1984

[30] Foreign Application Priority Data

Feb. 2, 1983 [JP] Japan ................... 58-15810

[51] Int. Cl.$^4$ ................................. C07J 1/00
[52] U.S. Cl. ....................... 260/397.4; 540/31
[58] Field of Search ............... 260/397.4, 239.55 C, 260/239.5

[56] References Cited

U.S. PATENT DOCUMENTS 2,356,154  8/1944  Fernholz .................... 260/239.55 C

FOREIGN PATENT DOCUMENTS 55-49398  4/1980  Japan ................... 260/397.4
55-51099  5/1980  Japan ................... 260/397.4

OTHER PUBLICATIONS

Chem. Abstracts vol. 93 (1980) Par. 132,688k.
Chem. Abstracts vol. 95 (1981) Par. 133,249w.

*Primary Examiner*—Elbert L. Roberts
*Attorney, Agent, or Firm*—Oblon, Fisher, Spivak, McClelland, & Maier

[57] ABSTRACT

A process of preparing radical anions which comprises reacting sodium and a polycyclic aromatic compound in a reaction solvent to prepare radical anions and supplying androstane-1,4-diene-3,17-dione-17-acetal into the obtained reaction mixture to reduce the same into an estrone acetal, characterized in that a solvent comprising polyethers having three or more ether bonds and maintained at a concentration higher than a predetermined value is used as the reaction solvent and the reaction is carried out at a temperature of from the melting point of sodium to 105° C. The process according to this invention can produce an estrone acetal at a high yield and with economical advantages in the industrial scale and the estrone acetal thus obtained is useful as an estrone precursor which is important as a female hormone.

5 Claims, No Drawings

PROCESS FOR PRODUCING AN ESTRONE ACETAL

DESCRIPTION

1. Technical Field

This invention concerns a process for producing an estrone acetal. More particularly, it relates to a process for producing an estrone acetal at a high yield and with economic advantages upon practicing in the industrial scale.

2. Background Art

Estrone acetal is one of important female hormones and is useful as a precursor of estrone as an intermediate to medicines for the therapy of prostatic hypertrophy and other steroid type medicines.

Heretofore, as a method of producing an estrone acetal from androstane-1,4-diene-3,17-dione-17-acetal (hereinafter abbreviated as "ADDK"), there is, for instance, a method as described in Japanese Patent Application Laid-Open No. 51099/1980 proposed by one of the present inventors.

The above-mentioned method concerns a process for producing estrone comprising preparing radical anions from sodium and a polycyclic aromatic compound in a mixed solvent of tetrahydrofuran and a small amount of polyether, then supplying a tetrahydrofuran solution of ADDK into the reaction mixture obtained to reduce ADDK into an estrone acetal and then deacetalizing the same.

However, this method should be regarded as an invention still at a fundamental stage, which can not attain a sufficient yield upon practicing in the industrial scale and which needs further investigation.

That is, according to the examples of this Laying-Open patent, 80–86% yield has been attained for estrone each by the case of the laboratory scale at gram order. However, when the method is practiced in the industrial scale, only about 40% yield can be attained even in the scale of about 25 liter, for example, as shown in Comparative Example 6 described hereinafter even under the conditions of Example 9 which attained the highest yield.

This invention improves the invention in the above-mentioned Laid-Open patent in view of the above and the object thereof is to provide a process for producing an estrone acetal at a high yield and with economical advantages upon practicing in the industrial scale.

DISCLOSURE OF INVENTION

The gist of this invention resides in a process for producing an estrone acetal which comprises preparing radical anions by reacting sodium and a polycyclic aromatic compound in a reaction solvent, and supplying a solution or slurry of androstane-1,4-diene-3,17-dione-17-acetal (hereinafter abbrevaited as "ADDK") prepared in a low boiling supplying solvent into the resultant reaction mixture and reducing the same into an estrone acetal, characterized in that (a) a solvent satisfying the conditions that:
  (i) polyethers containing three or more ether bonds are 1.5–5 times (v/w) of the total ADDK to be supplied,
  (ii) the concentration of said polyethers is not less than 35 (v/v) %,
  (iii) other solvent than said polyethers is not more than 5 (v/w) times of the total ADDK to be supplied, and
  (iv) the total amount of the reaction solvent is not less than 3 (v/w) times of the total ADDK, is used as the reaction solvent, (b) the temperatures for the preparing reaction of the radical anions and the reducing reaction of ADDK are from the melting point of sodium to 105° C., and (c) the ADDK supplying solvent is distilled out of the reaction system as required so that the reaction solvent can always maintain the above-mentioned conditions (ii)–(iv).

This invention is to be described specifically.

As the starting material, that is, ADDK for use in this invention there are mentioned, for example, an androstane-1,4-diene-3,17-dione-17,17-dialkylacetal represented by the general formula (I) and androstane-1,4-diene-3,17-dione-17-alkylene acetal represented by the general formula (II):

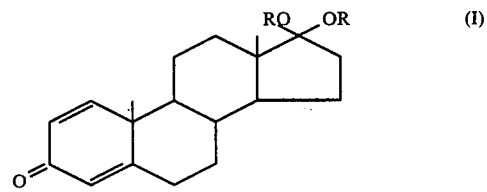

(wherein R represents a lower alkyl group with 1–6 carbon atom number),

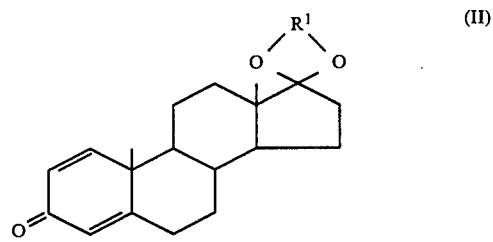

(wherein $R^1$ represents a lower alkylene group with 2–6 carbon atom number).

As specific examples of these ADDKs, there are mentioned, for instance, the following compounds: androstane-1,4-diene-3,17-dione-17,17-dimethylacetal, androstane-1,4-diene-3,17-dione-17,17-diethylacetal, androstane-1,4-diene-3,17-dione-17,17-dipropylacetal, androstane-1,4-diene-3,17-dione-17-ethyleneacetal, androstane-1,4-diene-3,17-dione-17-propyleneacetal.

While metallic sodium is usually employed as sodium, sodium alloys containing a small amount of other alkali metals or alkaline earth metals may be used so long as their melting points are lower than about 105° C. In such sodium alloys, in case the component of the alloys is potassium for instance, the content thereof up to about 20by weight may be tolerated.

The polycyclic aromatic compound usable as the radical anion precursor includes biphenyl, naphthalene, methylnaphthalene (two-isomers), dimethylnaphthalene (ten-isomers), ethylbiphenyl (three-isomers), phenanthrene, terphenyl (three-isomers), anthracene, acenaphthene, fluoranthene, dibenzofuran, benzophenone or the like, any of the isomers being usable.

Among them, most preferred are biphenyl, naphthalene, ethylbiphenyl, phenanthrene and terphenyl.

The polyethers having three or more ether bonds include, for example, the followings.

(a) Polyethylene glycol dialkyl ethers represented by the general formula (III)

$$R^2O(CH_2CH_2O)_nR^3 \quad (III)$$

(wherein $R^2$ and $R^3$ represent lower alkyl group and n represents an integer of 2 or greater). In the formula, $R^2$ and $R^3$ may be identical with each other. The polyethylene glycol dialkyl ether includes, for example, diglyme, triglyme, tetraglyme and pentaglyme.

(b) Polyethylene glycol monoalkyl ethers represented by the general formula (IV)

$$HO\text{-}(CH_2CH_2)_nR^4 \quad (IV)$$

(wherein $R^4$ represents a lower alkyl group and n represents an integer of 3 or greater).

(c) Cyclic polyether (also referred to as: crown ether) represented by the general formula (V)

$$(CH_2CH_2O)_m \quad (V)$$

(wherein m represents an integer of 4–6).

Examples of the cyclic polyether include, for example, 15-crown-5 (m=5) and 18-crown-6 (m=6).

As the ADDK supplying solvent for forming the solution or slurry of ADDK, a low boiling solvent is used, a solvent with a boiling point usually not higher than 110° C., preferably, not higher than 105° C. being used. Specifically mentioned are low boiling ether solvent such as tetrahydrofuran, dioxane and 1,2-dimethoxyethane (ethylene glycol dimethyl ether) and low boiling hydrocarbon solvent such as benzene and hexane, use of the low boiling ethereal solvent being preferred. 1,2-dimethoxyethane is particularly preferred.

One of the features of the process according to this invention is to carry out the preparing reaction of the radical anions and the reducing reaction of ADDK at a temperature of from the melting point of sodium to 105° C. By the adoption of such a temperature condition, sodium can be prevented from blocking and a high yield for the estrone acetal can be attained upon practicing in the industrial scale.

Specifically, according to the observation of the present inventors, the forming rate of the radical anions is in proportion to "the entire surface area of sodium per unit volume of the reaction system". Particles of sodium which have been dispersed previously are unexpectedly coagulated finally into a block in the case where the forming reaction of the radical anions is taken place at a temperature lower than the melting point of sodium. As the result, while "the entire surface area of sodium per unit volume of the reaction system" is significantly decreased by the change from the dispersed state to the blocked state, and the degree of decrease has no remarkable problem in the scale of the gram order, it increases with enlarging the scale of the reaction system. Accordingly, blocking of sodium greatly lowers the forming rate of the radical anions thereby making it difficult to form radical anions at a high concentration and reduces the yield of the estrone acetal upon practice in the industrial scale.

The above-described laid-open patent contains a general description with respect to the temperature of the reducing reaction for ADDK that it is usually between 30°–150° C. and, preferably, 60°–120° C. However, this description relevant to the reaction temperature is not stated as the result of careful investigations and discloses no useful technique for this invention.

That is, all of the examples in the above-mentioned laid-open patent uses the reaction temperature at the refluxing condition of tetrahydrofuran (66° C.) and nothing is mentioned at all to the blocking of sodium in its specification. In addition, as described, for example, in column 2, lines 36–42 of Japanese Patent Publication No. 10226/1967 (U.S. Pat. No. 3,274,182) as "high melting point of lithium and sodium prevents the melting of them in various organic solvents under the temperature in a refluxing range to control the contact of steroid to be converted", it has been considered to be a general procedure to use an alkali metal at such a temperature as it does not melt in order to maintain the initial dispersed state (particle size) of the alkali metal and carry out the predetermined reaction under control in the technical level at the time of filing this application. Referring further in connection therewith, there is no blocking problem, e.g., in the case of lithium and the predetermined dispersed state undergoes no substantial change even if lithium is used at a temperature not higher than its melting point and it is a phenomenon inherent to sodium that blocking is resulted when it is used at a level not higher than the melting point.

Furthermore, while the formation of radical anions at a high concentration is generally difficult at a high temperature and, for instance, the yield of estrone is extremely lowered as 30% at a temperature of 110°–115° C., as shown in the Comparative Example 4 described later, the general description for the reaction temperature in this laid-open patent also includes such a temperature which is considered meaningless.

The reaction temperature in the process according to this invention is a relatively higher temperature selected from the temperature range generally disclosed in the above-mentioned laid-open patent in order to maintain the sodium at a molten state. The use of such a high temperature condition, coupled with the condition of the reaction solvent as described later, enables to attain the object of this invention.

Specifically, one of other features of this invention resides in using, as a reaction solvent, a solvent satisfying the conditions that:

(i) polyethers having three or more ether bonds are 1.5–5 times (v/w) of the total ADDK to be supplied, (ii) the concentration of the polyethers is not less than 35 (v/v) %, (iii) other solvent than the polyethers is not more than 5 (v/w) times of the total ADDK to be supplied, and (iv) the total amount of the reaction solvent is not less than 3 (v/w) times of the total ADDK, and in that the ADDK supplying solution is distilled out of the reaction system as required so that the reaction solvent can always be maintained at the above-mentioned conditions (ii)–(iv).

Generally, it is difficult to form radical anions at a high concentration under the high temperature as adopted in the process according to this invention. Further, since the radical anions once formed are consumed in the reducing reaction of the ADDK, it is necessary to regenerate the radical anions at a high concentration within the reaction system in order to continue the reducing reaction.

Then, referring to the amount of the polyethers to be used, although it is relatively easy to prepare and regenerate the radical anions at a high concentration even under a relatively high temperature in the case where it is used in a large amount, it should be restricted to a range of 1.5–5 (v/w) times of ADDK upon practicing in the industrial scale due to the following reasons.

That is, while the general procedures of recovering the estrone usually involve an extracting procedure of adding an organic solvent insoluble to the reaction mixture and water in the same manner as the method described in the above-mentioned laid-open patent, the polyethers having three or more ether bonds dissolve estrone and have a compatibility with water. Accordingly, in a case where the amount of the polyethers to be used is in excess of the above-mentioned ratio, recovery loss is resulted due to the transfer of estrone to the aqueous phase to reduce the final estrone yield in the economically advantageous recovery procedure. In addition, the polyethers are generally expensive and the recovery thereof is difficult since they have high boiling point. Accordingly, it is economical to select the amount of the polyethers to be used from the range as described above.

Then, the use of the reaction solvent satisfying the foregoing conditions (ii) and (iii) is required in order to prepare and regenerate the radical anions at a high concentrations under a high reaction temperature condition employed in the process according to this invention, under the use of the polyethers in such a restricted amount. The condition (iii) is of a particular significance in the reducing reaction of ADDK in which the concentration of the polyether in the reaction solvent is gradually lowered by the ADDK supplying solvent and this indicates the allowable range as the solvent required for preparing the radical anions at a high concentration in the preparing reaction of the radical anions. Further, the condition (iv) defines the limit for the concentration of the slurry that can be stirred.

The above-mentioned laid-open patent contains a general description with respect to the amount of the polyether to be used that it is 5–50% based on the tetrahydrofuran, which is 5–20 (v/w) times of ADDK, and it contains the same portion as that in this invention with respect to the amount of the polyethers to be used to ADDK. However, the reaction solvent described in the above-mentioned laid-open patent does not simultaneously satisfy the above-mentioned condition (i) regarding the solvent of this invention that the amount of the polyethers is 1.5–5 (v/w) times of ADDK and the above-mentioned condition (ii) that the concentration of the polyethers is not less than 35 (v/v) %. Furthermore, there is described nothing at all for carrying out the reducing reaction of ADDK while distilling the ADDK supplying solvent out of the reaction system, which neither satisfies the above-described conditions (iii) with respect to the solvent according to this invention. For instance, the reaction is taken place while refluxing tetrahydrofuran, as described above, in each of the examples in the above-mentioned laid-open patent. Concretely, the reaction is carried out under reflux of tetrahydrofuran while supplying the solution of ADDK dissolved in tetrahydrofuran which is 5 (v/w) times of ADDK into the reaction solvent containing tetrahydrofuran 10 (v/w) times and polyether 2.5 (v/w) times of ADDK. That is, in the process as described in the above-mentioned laid-open patent, the radical anions are prepared in the reaction solvent in which the concentration of the polyethers is 20 (vol) % and the other solvent (tetrahydrofuran) than the polyether is 10 (v/w) times of ADDK, and regeneration of the radical anions and the reducing reaction of ADDK are carried out in the course where the value for the former is decreased to 14 (vol) % and the value for the latter is increased to 15 (v/w) times. Under such conditions of the reaction solvent, only a low estrone yield can be obtained even if the temperature conditions of this invention is employed, as shown in Comparative Examples 2 and 5 described later.

The amount of sodium metal to be used is usually 2–10 moles and, preferably, 3–8 moles per one mole of ADDK (providing that the molar amount of sodium consumed in the formation of alcoholate is excluded, in case polyethylene glycol monoalkyl ether represented by the formula (IV) is used as the polyethers).

The amount of the polycyclic aromatic compound to be used is usually 1–10 moles and, preferably, 1.5–8 moles based on one mole of ADDK.

The ratio of the ADDK supplying solvent to be used can be selected from a broad range and it is preferred to set the ratio not more than 20 (v/w) times of ADDK in view of the above-mentioned distillation load thereof and it is selected usually from the range of 2–15 (v/w) times.

The reaction is taken place while supplying the solution of slurry of ADDK into the reaction mixture containing the radical anions at such a rate that the color derived from the radical anions may not disappear. Further, the reaction is carried out under stirring in an inert gas atmosphere and the stirring is carried out so that the molten sodium is dispersed sufficiently. The time for supplying ADDK is selected from the range between 15 minutes and 5 hours.

While hydrocarbon solvents, ether solvents and the likes exemplified as the ADDK supplying solvent can be used as the other solvent that forms the reaction solvent together with the polyether having three or more ether bonds in this invention, preferred other solvent is an ether solvent, 1,2-dimethoxyethane being particularly preferred.

The sodium salt of the estrone acetal formed by contact between ADDK and radical anions can be converted into the estrone acetal by decomposing the radical anions and the excess sodium with methanol, ethanol, water or the like, thereafter, rendering the same acidic by an appropriate mineral acid or organic acid.

In the case of using ADDK represented by the above-mentioned general formula (I), an estrone acetal as represented by the general formula (VI) is obtainable:

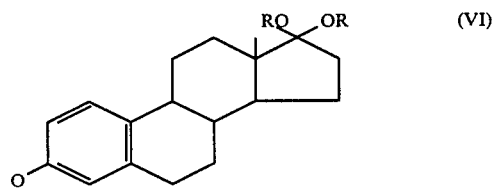

(wherein R has the same meaning as above). Further, in the case of using ADDK represented by the above-mentioned general formula (II), a product represented by the general formula (VII) can be obtained.

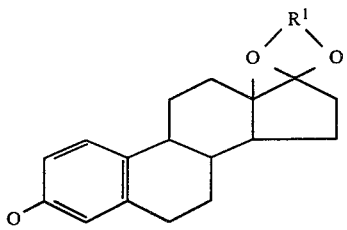

(wherein R[1] has the same meaning as above).

The estrone acetal can completely be deacetalized by heating as it is (in the presence of an acid catalyst) to thereby produce estrone.

Examples of the acid usable herein are hydrochloric acid, sulfuric acid and p-toluene sulfonic acid.

In the process according to this invention, it is possible to prevent the blocking of sodium and prevent the decrease in the radical anions, whereby improvement in the estrone yield can be attained. This effect becomes remarkable particularly upon practicing in a large scale, in which industrial value of this invention can be found.

Best Mode of Carrying Out the Invention

This invention will further be explained specifically referring to examples, but the invention is no way limited to the following examples so long as it does not go beyond the purport thereof.

"ADDK" used in the following Examples and Comparative Examples means androstane-1,4-diene-3,17-dione-17-ethyleneacetal.

EXAMPLE 1

When a mixture of 3.36 kg of sodium (146 gr-mole), 15.0 kg of biphenyl (97.4 gr-mole), 16.0 liters of diglyme and 20.0 liters of 1,2-dimethoxyethane was heated at 98°–102° C. while stirring in a nitrogen atmosphere, the liquid reaction mixture exhibited deep green color. After continuing the stirring for 30 min, a solution of 8.0 kg (24.4 gr-mole) of ADDK in 80.0 liters of 1,2-dimethoxyethane was gradually supplied at such a rate that the deep green color did not disappear while keeping the reaction temperature at 98°–102° C. (the supplying rate was controlled corresponding to the distilling rate of 1,2-dimethoxyethane distilled out of the system, required time 1.5 hours). Then, 50 kg of water were gradually supplied under a nitrogen gas stream. After cooling to the room temperature, 20.5 kg of concentrated hydrochloric acid were added gradually. The thus obtained liquid mixture was mixed under heating at 60°–65° C. for one hour. After cooling to the room temperature, 7.99 kg of an aqueous 25 wt % sodium hydroxide solution were added while stirring for neutralization. Then, it was separated into an organic phase and an aqueous phase by settling for about 30 min. The aqueous phase was extracted with 40 liters of tetrahydrofuran. The tetrahydrofuran solution thus obtained was joined with the organic phase and concentrated under a reduced pressure. 80 liters of heptane, 8 liters of toluene and 40 liters of water were added to the residue and stirred at 80° C. for one hour. After leaving at a room temperature over one night, crystals were collected by filtration, washed with water and dried to obtain crude crystals of estrone. Estrone yield 5.92 kg (90.0 mole % yield).

EXAMPLE 2

Experiment was carried out under the same conditions as those in Example 1 except for using tetraglyme instead of diglyme as the polyethers to obtain estrone at 88 mole % yield.

EXAMPLE 3

Experiment was carried out in the same procedures as those in Example 1 while using ethylbiphenyl as a radical anion precursor.

When a mixture of 3.59 kg of sodium (156 gr-mole), 13.3 kg of ethylbiphenyl (73.1 gr-mole), 16.0 liters of diglyme and 20.0 liters of 1,2-dimethoxyethane was heated at 98°–102° C. while stirring under a nitrogen atmosphere, the liquid reaction mixture exhibited deep green color. After continuing the stirring for 30 min, a solution of 8.0 kg of ADDK (24.4 gr-mole) in 80 liters of 1,2-dimethoxyethane was supplied at such a rate that the deep green color did not disappear while corresponding to the rate of 1,2-dimethoxyethane distilling out of the system (reaction temperature 98°–102° C., required time 1.0 hour). After applying the same post treatment as in Example 1, estrone was obtained at 85 mole % of yield.

EXAMPLE 4

When a mixture of 3.59 kg of sodium (156 gr-mole), 22.5 kg of biphenyl (146 gr-mole) and 40.0 liters of diglyme was heated at 98°–102° C. while stirring under a nitrogen atmosphere, the liquid reaction mixture exhibited deep green color. After continuing the stirring for 30 min, a solution of 8.0 kg of ADDK dissolved in 40.0 liters of tetrahydrofuran was supplied at such a rate that the deep green color did not disappear while corresponding to the distillating rate of tetrahydrofuran distilled out of the system (reaction temperature 98°–102° C., required time 0.75 hour, tetrahydrofuran recovery amount ca. 32 liters). After applying the post procedure in the same manner as in Example 1, estrone was obtained at 86 mole % of yield.

EXAMPLE 5

Experiment was carried out under the same conditions as those in Example 4 except for replacing the ADDK supplying solvent from tetrahydrofuran to benzene (amount used : 40 liters) (amount of benzene distilled after supplying ADDK; ca. 28 liters) estrone was obtained at 83 mole % of yield.

EXAMPLE 6

When a mixture of 4.80 kg of sodium/potassium alloy (potassium 20 wt %) (Na=167 gr-mole, K=24.6 gr-mole), 15.0 kg of biphenyl (97.4 gr-mole), 28.0 liters of diglyme and 40.0 liters of 1,4-dioxane was heated at 98°–104° C. while stirring under nitrogen atmosphere, the liquid reaction mixture exhibited deep green color. After continuing the stirring for 30 min, a solution of 8.0 kg of ADDK dissolved in 80 liters of 1,4-dioxane was gradually supplied at such a rate that the deep green color did not disappear while corresponding to the distillating rate of 1,4-dioxane out of the system (reaction temperature 101°–104° C., required time 1.0 hour).

After applying the post procedure in the same manner as in Example 1, estrone was obtained at 85 mole % of yield.

EXAMPLE 7

Experiment was carried out under the same conditions as those in Example 1 except for decreasing the amount of diglyme to be used from 16.0 liters to 12.0 liters to obtain estrone at 83 mole % of yield.

COMPARATVE EXAMPLE 1

Experiment was carried out under the same conditions as those in Example 1 except that the amount of diglyme to be used was decreased from 16.0 liters to 8.0 liters. Estrone yield was 67 mole %.

COMPARATIVE EXAMPLE 2

After preparing radical anions under the same conditions as those in Example 1, ADDK was supplied without distilling the supplying solvent, 1,2-dimethoxyethane, out of the system (reaction temperature 98°–102° C., reaction pressure: normal pressure—1.0 Kg/cm$^2$G, time required for supplying ADDK: 1.5 hours). The estrone yield was 70 mole %.

COMPARATIVE EXAMPLE 3

The reaction was taken place under the same conditions as those in Example 1 except for changing the reaction temperature to 110°–115° C. The estrone yield was 60 mole %.

COMPARATIVE EXAMPLE 4

The reaction was carried out under the same conditions as those in Example 9 of Japanese Patent Application Laying-Open No. 51099/1980 except for changing the reaction temperature from the tetrahydrofuran reflux temperature (66° C.) to 110°–115° C.

Specifically, when 0.92 g of sodium (40 mmole) and 5.55 g of biphenyl (36 mmole) were added to a solution of 20 ml of tetrahydrofuran and 5 ml of diglyme, and heated at 110° C. while stirring in an argon gas stream, the liquid reaction mixture exhibited deep green color (pressure 2.5 Kg/cm$^2$G). A solution of 1.971 g (6 mmole) of ADDK in 10 ml of tetrahydrofuran was dropped while maintaining the reaction temperature at 110°–115° C. without distilling the tetrahydrofuran out of the system (required time: 50 min, pressure: 2.5 Kg/cm$^2$G). However, it was difficult to always maintain the black green color of the liquid reaction mixture in the course of supplying ADDK under this temperature condition. After the dropping has been completed, post treatment was carried out in accordance with the conventional manner (the same method as in Example 1) to isolate estrone (yield 30 mole %).

COMPARATIVE EXAMPLE 5

The reaction was carried out under the same conditions as those in Example 9 of Japanese Patent Application Laying-Open No. 51099/1980 except for changing the reaction temperature from the reflux temperature of tetrahydrofuran (66° C.) to 98°–102° C.

Specifically, when 0.92 g (40 mmole) of sodium and 5.55 g (36 mmole) of biphenyl were added to a solution of 20 ml of tetrahydrofuran and 5 ml of diglyme, and heated to 98°–102° C. while stirring in an argon gas stream, the liquid reaction mixture exhibited deep green color. A solution of 1.971 g (6 mmole) of ADDK in 10 ml of tetrahydrofuran was dropped at a reaction temperature of 98°–102° C. without distilling tetrahydrofuran out of the system (required time: 1.0 hour). After the dropping, post treatment was applied in the same manner as in Example 1 to isolate estrone (yield: 65 mole %).

COMPARATIVE EXAMPLE 6

This Comparative Example is such an experiment where the experiment in Example 9 of Japanese Patent Application Laid-Open No. 51099/1980 was scaled up from 1.971 g (6×10$^{-3}$ gr-mole) to 328 g (1 gr-mole) of ADDK.

When 513 g of 30% by weight of sodium dispersion (sodium 154 gr (6.7 gr-mole)) previously prepared in toluene solvent, 3.3 liters of tetrahydrofuran, 0.82 l of diglyme and 924 gr of biphenyl (6 gr-mole) were successively added and heated under reflux in a nitrogen gas stream while stirring, the liquid reaction mixture exhibited deep green color. However, as the solution exhibited intense deep green color, sodium particles dispersed so far were coagulated into a block, thereby the stirring was obliged to interrupt occasionally. Then, a solution of 328 g (1 gr-mole) of ADDK dissolved in 1.6 liters of tetrahydrofuran was supplied for one hour at such a rate that the deep green color did not disappear at the reflux temperature of tetrahydrofuran (66° C.). After the completion of the supply, it was refluxed under heating for 10 min, cooled to the room temperature, and then gradually admixed with 2.5 liters of water in a nitrogen gas stream. Post treatment was applied in the same manner as in Example 1 to isolate estrone (yield 40 mole %).

The results for the Examples 1–7, as well as the Comparative Examples 1–6 as described above are collectively shown in Table 1 and Table 2 respectively.

TABLE 1

| Example | Amount of polyether used (V/W-ADDK) | Other solvent*1 Type*3 | Other solvent*1 Amount used (V/W-ADDK) | ADDK supplying solvent Type*3 | ADDK supplying solvent Amount used (V/W-ADDK) | Presence or absence of distillate | Reaction temperature (°C.) | Polyether concentration*2 Start (vol. %) | Polyether concentration*2 End (vol. %) | Estrone Yield (mole %) |
|---|---|---|---|---|---|---|---|---|---|---|
| 1$^{a,b}$ | 2$^d$ | DME | 2.5 | DME | 10 | yes | 98–102 | 44 | ca. 44 | 90 |
| 2$^{a,b}$ | 2$^e$ | DME | 2.5 | DME | 10 | yes | 98–102 | 44 | ca. 44 | 88 |
| 3$^{a,c}$ | 2$^d$ | DME | 2.5 | DME | 10 | yes | 98–102 | 44 | ca. 44 | 85 |
| 4$^{a,b}$ | 5$^d$ | — | — | THF | 5 | yes | 98–102 | 100 | ca. 83 | 86 |
| 5$^{a,b}$ | 5$^d$ | — | — | BZ | 5 | yes | 98–102 | 100 | ca. 77 | 83 |
| 6$^{a,b}$ | 3.5$^d$ | DON | 5 | DON | 10 | yes | 101–104 | 41 | ca. 41 | 85 |

TABLE 1-continued

| Example | Amount of polyether used (V/W-ADDK) | Other solvent[*1] Type[*3] | Amount used (V/W-ADDK) | ADDK supplying solvent Type[*3] | Amount used (V/W-ADDK) | Presence or absence of distillate | Reaction temperature (°C.) | Polyether concentration[*2] Start (vol. %) | End (vol. %) | Estrone Yield (mole %) |
|---|---|---|---|---|---|---|---|---|---|---|
| 7[a,b] | 1.5[d] | DME | 2.5 | DME | 10 | yes | 98–102 | 38 | ca. 38 | 83 |

[*1]Reaction solvent coexistent with polyether in the step for preparing the radical anion.
[*2]Polyether concentration (vol. %) = [polyether (l)/(polyether (l) + other solvent (l))] × 100
[*3]Abbreviation for solvent
DME: (1,2-dimethoxyethane)
THF: (tetrahydrofuran)
DON: (1,4-dioxane)
BZ: (benzene)
[a]8 kg ADDK charged,
[b]biphenyl used,
[c]ethyl biphenyl used,
[d]diglyme,
[e]tetraglyme

TABLE 2

| Comparative Example | Amount of polyether used (V/W-ADDK) | Other solvent[*1] Type[*3] | Amount used (V/W-ADDK) | ADDK supplying solvent Type[*3] | Amount used (V/W-ADDK) | Presence or absence of distillate | Reaction temperature (°C.) | Polyether concentration[*2] Start (vol. %) | End (vol. %) | Estrone Yield (mole %) |
|---|---|---|---|---|---|---|---|---|---|---|
| 1[a,d] | 1 | DME | 2.5 | DME | 10 | yes | 98–102 | 29 | ca. 29 | 67 |
| 2[a,d] | 2 | DME | 2.5 | DME | 10 | no | 98–102 | 44 | ca. 14 | 70 |
| 3[a,d] | 2 | DME | 2.5 | DME | 10 | yes | 110–115 | 44 | ca. 44 | 60 |
| 4[b,d] | 2.5 | THF | 10 | THF | 5 | no | 110–115 | 20 | 14 | 30 |
| 5[b,d] | 2.5 | THF | 10 | THF | 5 | no | 98–102 | 20 | 14 | 65 |
| 6[c,d] | 2.5 | THF | 10 | THF | 5 | no | 66 | 20 | 14 | 40 |
| Cf.[*4b,d] | 2.5 | THF | 10 | THF | 5 | no | 66 | 20 | 14 | 86.1 |

[*1]Reaction solvent coexistent with polyether in the step for preparing the radical anion.
[*2]Polyether concentration (vol. %) = [polyether (l)/(polyether (l) + other solvent (l))] × 100
[*3]Abbreviation for solvent:
DME: (1,2-dimethoxyethane)
THF: (tetrahydrofuran)
[*4]Example 9 in Japanese Patent Application Laid-Open No. 51099/1980
[a]8 kg ADDK charged,
[b]1,971 gr ADDK charged,
[c]328 gr ADDK charged,
[d]biphenyl used,
[e]diglyme

INDUSTRIAL APPLICABILITY

The process according to this invention is useful as a method for producing an estrone acetal as an estrone precursor in the industrial scale. And estrone is one of important female hormones and is a useful substance as an intermediate to medicines for the therapy of prostatic hypertrophy and other steroid type medicines.

We claim:

1. A process for producing an estrone acetal which comprises reacting sodium and a polycyclic aromatic compound in a reaction solvent on an industrial scale of at least 25 liters to prepare radical anions and supplying a solution or slurry of androstane-1,4-diene-3,17-dione-17-acetal, hereinafter abbreviated as ADDK, prepared in a low boiling supplying solvent into the thus obtained reaction mixture to thereby reduce the same into an estrone acetal, wherein
    (a) said reaction solvent satisfies the conditions that:
        (i) said reaction solvent contains a polyether or mixture of polyethers having three or more ether bonds and said polyethers are present at 1.5–5 (v/w) times the total ADDK to be supplied,
        (ii) the concentration of said polyethers is not less than 35 (v/v) %,
        (iii) said reaction solvent optionally contains a solvent other than said polyethers which is present at not more than 5 (v/w) times the total ADDK to be supplied, and
        (iv) the total amount of the reaction solvent is not less than 3 (v/w) times the total ADDK to be supplied;
    (b) the temperatures for the preparing reaction of radical anions and the reducing reaction of ADDK are maintained in the range from the melting point of sodium to 105° C.; and
    (c) the supplying solvent of ADDK is distilled out of the reaction system as required so that the reaction solvent can always maintain the foregoing conditions (ii)–(iv).

2. The process for producing the estrone acetal as defined in claim 1, wherein the reaction solvent is an ethereal solvent comprising polyethers having three or more ether bonds and other ether than above.

3. The process for producing the estrone acetal as defined in claim 2, wherein said other ether is 1,2-dimethoxyethane.

4. The process for producing the estrone acetal as defined in claims 2, 3, and 1 wherein the supplying solvent of ADDK is a solvent comprising ethers.

5. The process for producing the estrone acetal as defined in claim 4, wherein the ethers are 1,2-dimethoxyethane.

* * * * *